United States Patent [19]

Behl

[11] Patent Number: 5,552,153
[45] Date of Patent: Sep. 3, 1996

[54] PHARMACEUTICAL COMPOSITION FOR TRANSDERMAL DELIVERY

[75] Inventor: Charanjit R. Behl, Nutley, N.J.

[73] Assignee: Hoffman-La Roche Inc., Nutley, N.J.

[21] Appl. No.: 234,216

[22] Filed: Apr. 28, 1994

[51] Int. Cl.$^6$ .............. A61K 9/70; A61F 13/00; A61L 15/10
[52] U.S. Cl. ............ 424/449; 514/784; 514/785; 514/786; 514/946; 514/947; 514/969
[58] Field of Search .................................. 424/449

[56] References Cited

U.S. PATENT DOCUMENTS

| | | | |
|---|---|---|---|
| 4,537,776 | 8/1985 | Cooper | 514/424 |
| 4,557,934 | 12/1985 | Cooper | 424/128 |
| 4,626,539 | 12/1986 | Aungst et al. | 514/282 |
| 4,719,239 | 1/1988 | Muller et al. | 514/785 |
| 4,722,941 | 2/1988 | Eckert et al. | 514/784 |
| 4,837,025 | 6/1989 | Guillemet et al. | 424/448 |
| 4,863,970 | 9/1989 | Patel et al. | 514/784 |
| 4,879,297 | 11/1989 | Mahjour et al. | 514/282 |
| 4,885,174 | 12/1989 | Bodor et al. | 424/449 |
| 5,069,909 | 12/1991 | Sharma et al. | 424/449 |
| 5,096,715 | 3/1992 | Sinclair | 424/449 |
| 5,176,916 | 1/1993 | Yamanaka et al. | 424/448 |
| 5,234,957 | 8/1993 | Mantelle | 514/772.6 |
| 5,296,222 | 3/1994 | Petersen et al. | 424/94.63 |
| 5,332,576 | 7/1994 | Mantelle | 424/443 |
| 5,352,457 | 10/1994 | Jenkins | 424/448 |
| 5,362,497 | 11/1994 | Yamada et al. | 424/449 |
| 5,378,473 | 1/1995 | Sharma et al. | 424/449 |

FOREIGN PATENT DOCUMENTS 0159167  4/1985  European Pat. Off. .

*Primary Examiner*—Shep K. Rose
*Attorney, Agent, or Firm*—George W. Johnston; Ellen Ciambrone Coletti

[57] ABSTRACT

A pharmaceutical composition for transdermal delivery comprising an effective amount of an active ingredient selected from a benzodiazepine and a benzodiazepine antagonist; ethanol; caprylic acid; and oleic acid. Additionally, the composition may contain silicon fluid, benzyl alcohol, transcutol or dimethyl sulfoxide.

35 Claims, No Drawings

PHARMACEUTICAL COMPOSITION FOR TRANSDERMAL DELIVERY

BACKGROUND OF THE INVENTION

Benzodiazepines are used as sedative hypnotics, in the treatment of anxiety disorders and in the treatment of seizures.

Benzodiazepine antagonists, such as, flumazenil, are used for a complete or partial reversal of the sedative effects of benzodiazepines and for the management of benzodiazepine overdose.

Benzodiazepines and benzodiazepine antagonists, are administered either via gastrointestinal tract or parenterally. Alternatively, a transdermal route of drug delivery can be used. Generally, the most critical problem in this route is the lack of adequate absorption of drugs through the skin. Some chemical substances can improve this absorption and are called absorption enhancers. Previous studies involving a transdermal delivery system of benzodiazepines include the use of an ointment formulation containing the absorption enhancers Azone® and sorbitan monoleate, see, for example, Ogiso, et al, *Percutaneous Absorption of Clonazepam in Rabbit*, Chem. Pharm. Bull. 37(2), pgs. 442–445 (1989); Ogiso, et al, *Membrane-Controlled Transdermal Therapeutic System Containing Clonazepam and Anticonvulsant Activity After Its Application*, Chem. Pharm. Bull. 37(2) pgs. 446–449 (1989) and an alcohol based formulation, see, Kumar et al. In Vitro Transdermal Delivery of $^{14}$C-Clonazepam Across Hairless Guinea Pig, Pharmaceutical Research, Volume 8, No. 10, October 1991 (Supplement) p. S-205.

SUMMARY OF THE INVENTION

The present invention relates to a pharmaceutical composition for transdermal delivery comprising an effective amount of an active ingredient selected from a benzodiazepine and benzodiazepine antagonist; ethanol; caprylic acid; and oleic acid.

DETAILED DESCRIPTION OF THE INVENTION

The present invention relates to a pharmaceutical composition for transdermal delivery comprising an effective amount of an active ingredient selected from a benzodiazepine and benzodiazepine antagonist; ethanol; caprylic acid; and oleic acid with or without an inert carrier.

As used herein, the term benzodiazepine means any active pharmaceutical compound in the benzodiazepine family, such as, diazepam, chlordiazepoxide, fluazepam, lorazepam and clonazepam, preferably clonazepam.

As used herein the term benzodiazepine antagonist means any compound antagonistic to benzodiazepines, such as, preferably flumazenil.

Preferably, ethanol is present in the composition of the invention in the range of from about 10 to about 95 percent by weight of the composition. In a particularly preferred embodiment, ethanol is present in the composition in the range of from about 24 to about 90 percent by weight of the composition.

Preferably, caprylic acid is present in the composition of the invention in the range of from about 1 to about 10 percent by weight of the composition, particularly preferred at about 3 percent.

Preferably, oleic acid is present in the composition in the range of from about 1 to about 10 percent by weight of the composition, particularly preferred at about 3 percent.

When the active ingredient is a benzodiazepine antagonist, such as flumazenil, preferably, ethanol is present in the composition in an amount of from about 10 to about 95 percent by weight of the composition; particularly preferred in an amount of from about 50 to about 70 percent; caprylic acid is present in the composition in an amount of from about 1 to about 10 percent by weight of the composition, particularly preferred in an amount of from about 3 to 5 percent; and oleic acid is present in the composition in an amount of from about 1 to about 10 percent by weight of the composition, particularly preferred in an amount of from about 3 to 5 percent.

When the active ingredient is a benzodiazepine, such as clonazepam, preferably, ethanol is present in the composition in an amount of from about 10 to about 95 percent by weight of the composition, particularly preferred in an amount of from about 50 to 90 percent; caprylic acid is present in the composition in an amount of from about 1 to about 10 percent by weight of the composition, particularly preferred at about 3 percent; and oleic acid is present in the composition in an amount of from about 1 to about 10 percent by weight of the composition, particularly preferred at about 3 percent.

The described pharmaceutical composition may contain additional enhancing materials such as, for example, silicon fluid such as Silicon Dow® 556 (polyphenyl methyl siloxane), preferably in the range of from about 15 to about 25 percent by weight of the composition, particularly preferred at about 20 percent; dimethylsulfoxide, preferably in the range of from about 1 to about 20 percent by weight of the composition, particularly preferred at about 2 percent; acetone, preferably in the range of from about 15 to about 25 percent by weight of the composition, particularly preferred at about 20 percent; caprylic/capric triglyceride such as Miglyol® 840 (propylene glycol diesters of saturated vegetable fatty acids of the chain lengths $C_8$–$C_{10}$, particularly 2% max caproic acid ($C_{6:0}$), 65–80% caprylic acid ($C_{8:0}$), 15–30% capric acid ($C_{10:0}$), and 3% max. linoleic acid ($C_{18:2}$) Dynamit Nobel), preferably in the range of from about 25 to about 40 percent by weight of the composition, particularly preferred at about 36 percent; transcutol (diethylene glycol monoethyl ether from Gattefasse) preferably in the range of from about 15 to about 30 percent by weight of the composition, particularly preferred at about 20 percent; and benzyl alcohol, preferably in the range of from about 5 to about 15 percent by weight of the composition, particularly preferred at about 10 percent.

Pharmaceutical compositions in accordance with this invention can be formulated to additionally contain conventional additives or supplementary ingredients in the usual amounts for such materials. The composition can be in the form of a gel, as well as, in the form of a solution, preferably a thickened solution. By way of illustration such additives or supplements include the following.

Gelling agents which can be used include, for example, hydroxy methyl cellulose, preferably in the range of from 1 to 4 percent by weight of the composition; tragacanth preferably in the range of from 2 to 5 percent by weight of the composition; sodium alginate, preferably in the range of from 2 to 10 percent by weight of the composition; gelatin, preferably in the range of from 2 to 15 percent by weight of the composition; methylcellulose, preferably in the range of from 2 to 4 percent by weight of the composition; sodium carboxymethylcellulose, preferably in the range of from 2 to 5 percent by weight of the composition; and polyvinyl alcohols, preferably in the range of from 10 to 20 percent by weight of the composition. A particularly preferred gelling agent is Klucel®.

Klucel HF is a hydroxypropyl cellulose (Hercules Inc.) with a molecular weight in the 1,000,000 range and moisture content of 17% for 1,500–2,500. Hydroxypropyl cellulose is preferably present in the composition in the range of from 1.0 to 5.0 percent by weight, particularly preferred in the range of from 1.0 to 4.0 percent by weight. Generally, enough Klucel is added to provide a reasonably good gel-consistency to the product.

The preservatives which can be used in the invention include, for example, parabens, preferably at about 0.2%; benzoic acid, preferably at about 0.2%; and, chlorocresol, preferably at about 0.1%.

If needed, antioxidants can be used in the gel formulations to improve the stability of the drug. These antioxidants include, for example, ascorbyl palmirate, butylated hydroxyanisole, butylated hydroxytoluene, potassium sorbate, sodium bisulfate, sorbic acid, propyl gallate and sodium metabisulfite.

Preferably, the pharmaceutical composition of the invention is administered to a host in need of such treatment in a transdermal patch of a reservoir type.

Adhesives used in making transdermal patches for use with the invention include, for example, preferably polyisobutylene, silicone based adhesives and acrylic polymers. The adhesive polymers can be mixed with other excipients such as mineral oil to make them more suitable for a given purpose.

The backing membrane of a transdermal patch constitutes the upper part (exposed to the environment) of a transdermal patch and is made of materials such as, for example, preferably polyester films, ethyl vinyl acetate, polypropylene, polyethylene and polyvinyl-chloride.

A rate controlling membrane of a transdermal patch is placed in contact with the pharmaceutical composition of the invention and its other side is in contact with the skin of a host. The rate controlling membrane is made of materials such as, for example, preferably, dimethylpolysiloxane, polyacetate, polyurethane and ethylene-vinyl acetate copolymer and polypropylene.

At the bottom of a transdermal patch, a protective liner is placed in contact with the adhesive layer. This liner protects against the drug release from the formulation reservoir until the liner is peeled off the patch and applied on the skin surface of the host. Such liners are made of materials including preferably polyethylene terephthalate film, polyester membrane and polycarbonate film.

Alternatively, one can make transdermal patches which are called monolithic or adhesive type patches. In this case, the drug is dispersed either in a suitable adhesive or in a suitable non-adhesive polymer and then the mixture is layered onto a membrane. A protective membrane is placed on the adhesive.

In vivo tests were utilized to evaluate the absorption of benzodiazepines and benzodiazepine antagonists administered in accordance with this invention.

Methods

General Procedure:

Hairless guinea pigs (HGP) were anesthetized by using Ketamin-HCl and promazine. The side sites of the animals were cleaned with water. Zero time blood samples were withdrawn from the ocular site. The transdermal drug delivery systems were placed on the skin, two per animal providing a total area of 9.0 to 10.0 sq. cm., precisely measured. The animals were allowed to come out of anesthesia in between blood samples. Blood samples were withdrawn at 1.0, 2.0, 3.0, 4.0, and 6.0 hours. The blood was allowed to clot and then centrifuged to obtain serum. The drug concentration was determined by using an HPLC method. After the last sample point, the transdermal drug delivery system was removed from the animal's skin and the site was examined for any "obvious" signs of irritation/reddening.

Serum Collection:

The animals were bled from the eye into Microtainer serum separator tubes (Becton Dickinson, 5960). The blood (0.6 mL) was centrifuged at 4,000 rpm for 15 minutes (4,400 g) on a Beckman J-6M centrifuge with a JS-4.2 rotor. Serum was separated and frozen until the HPLC analysis. Before sample preparation, the serum was thawed and centrifuged again.

Sample Preparation:

Two hundred and fifty microliters of serum were mixed with 250 mcL of water and 25 mcL of an internal standard, flunitrazepam 1 mcg/mL in methanol, were added. The sample was purified on a solid phase mini column, Adsorbex RP-18 (100 mg; EM Science) using the sample preparation unit Adsorbex SPU). The columns were treated before with 2 mL of methanol and washed with 4 mL of water. Samples were applied and the columns were washed with 4 mL of water. The columns were dried under vacuum (5" Hg) and eluted with two portions of 125 mcL of acetonitrile:water (1:1).

HPLC Conditions:

Samples were analyzed on a Waters HPLC system using Waters 600E controller, Waters 712 WISP automatic sample injector and Applied Biosystems 785A programmable absorbance detector.

| Column: | Waters Nova Pak C18, 75 × 3.9 mm |
|---|---|
| Flow rate: | 2.0 mL/min |
| Mobile Phase: | 25% acetonitrile in water (v/v) |
| Wavelength: | 310 nm |
| Data collection: | 2 points/sec, 1 V/AU, A/D = 0.1, rise time = 1 sec |
| Injection volume: | 100 mcL |
| Run time: | 15 min/sample |

The retention times of the internal standard, flunitrazepam, and clonazepam or flumazenil were 5.5 and 4.5 minutes, respectively. The HPLC system is connected to a computer where a program was used to determine the area under the curve of the drug and the internal standard.

Lack of Interference:

The chromatogram of the HGP serum shows no peak at the retention time of clonazepam indicating an interference free detection of the drug.

Sensitivity and Linearity of Response:

A standard curve was made by adding clonazepam or flumazenil and the internal standard to HGP serum. A linear relationship was observed between the observed response and concentration of clonazepam in the range of 5 to 500 ng/mL. The recovery of the drug in these experiments was 75±15%, and was corrected using the internal standard. Apparent limit of quantification was found to be about 5 ng/mL of clonazepam or flumazenil in the HGP serum.

Data Analysis:

The HPLC data were computed in terms of drug concentration per unit volume of the serum and were plotted as a function of time. In such experiments, the blood levels are expected to rise to a maximum and then decline due to a decrease in the chemical potential of the drug in the patch. No rate controlling membrane was placed at the bottom of the contemporary transdermal delivery dosage system.

Results

| Formulation[a] | Max Blood Level Observed in HGP (ng/ml) |
|---|---|
| Example 1 | 130 |
| Example 2 | 90 |
| Example 3 | 80 |
| Example 4 | 300 |
| Example 5 | 37 |
| Example 6 | 525 |
| Example 7 | 470 |
| Example 8 | 225 |
| Example 9 | 273 |
| Control A[b] | 33 |
| Control B[c] | 15 |

[a]Dose was 12 mg per animal applied to an area of 9 cm sq.
[b]Control A contained 11 mg of clonazepam in a formulation comprised of 97% ethanol and 3% Klucel HF applied to an area of 9.8 cm$^2$
[c]Control B contained 12 mg of flumazenil in a formulation comprised of 97% ethanol and 3% Klucel HF applied to an area of 5.0 cm$^2$.

By way of illustration, some suitable pharmaceutical compositions in accordance with this invention are set forth below. While clonazepam and flumazenil, the preferred benzodiazepine and benzodiazepine antagonist for this invention, are used to illustrate the compositions, it should be understood that other benzodiazepine and benzodiazepine antagonists may be substituted in appropriate amounts.

EXAMPLE 1

| | |
|---|---|
| Clonazepam | 0.010 Gm |
| Ethanol | 0.900 Gm |
| Caprylic Acid | 0.030 Gm |
| Oleic Acid | 0.030 Gm |
| Klucel HF | 0.030 Gm |
| Total | 1.000 Gm |

EXAMPLE 2

| | |
|---|---|
| Clonazepam | 0.010 Gm |
| Ethanol | 0.702 Gm |
| Silicon Fluid | 0.198 Gm |
| Caprylic Acid | 0.030 Gm |
| Oleic Acid | 0.030 Gm |
| Klucel HF | 0.030 Gm |
| Total | 1.000 Gm |

EXAMPLE 3

| | |
|---|---|
| Clonazepam | 0.010 Gm |
| Ethanol | 0.800 Gm |
| Benzyl Alcohol | 0.100 Gm |
| Caprylic Acid | 0.030 Gm |
| Oleic Acid | 0.030 Gm |
| Klucel HF | 0.030 Gm |
| Total | 1.000 Gm |

EXAMPLE 4

| | |
|---|---|
| Clonazepam | 0.010 Gm |
| Ethanol | 0.600 Gm |
| Silicon Fluid | 0.200 Gm |
| Benzyl Alcohol | 0.100 Gm |
| Caprylic Acid | 0.030 Gm |
| Oleic Acid | 0.030 Gm |
| Klucel HF | 0.030 Gm |
| Total | 1.000 Gm |

EXAMPLE 5

| | |
|---|---|
| Clonazepam | 0.010 Gm |
| Ethanol | 0.510 Gm |
| Transcutol | 0.200 Gm |
| Silicon Fluid | 0.200 Gm |
| Caprylic Acid | 0.030 Gm |
| Oleic Acid | 0.030 Gm |
| Klucel HF | 0.020 Gm |
| Total | 1.000 Gm |

EXAMPLE 6

| | |
|---|---|
| Flumazenil | 0.010 Gm |
| Ethanol | 0.710 Gm |
| Silicon Dow 556 | 0.20 Gm |
| Caprylic Acid | 0.03 Gm |
| Oleic Acid | 0.03 Gm |
| Klucel HF | 0.02 Gm |
| Total | 1.000 Gm |

EXAMPLE 7

| | |
|---|---|
| Flumazenil | 0.010 Gm |
| Ethanol | 0.690 Gm |
| Silicon Dow 556 | 0.200 Gm |
| Dimethyl Sulfoxide | 0.020 Gm |
| Oleic Acid | 0.030 Gm |
| Caprylic Acid | 0.030 Gm |
| Klucel HF | 0.020 Gm |
| Total | 1.000 Gm |

EXAMPLE 8

| | |
|---|---|
| Flumazenil | 0.010 Gm |
| Ethanol | 0.510 Gm |
| Acetone | 0.200 Gm |
| Silicon Dow 556 | 0.200 Gm |
| Caprylic Acid | 0.030 Gm |
| Oleic Acid | 0.030 Gm |
| Klucel HF | 0.020 Gm |
| Total | 1.000 Gm |

EXAMPLE 9

| | |
|---|---|
| Flumazenil | 0.010 Gm |
| Ethanol | 0.24 Gm |
| Transcutol | 0.250 Gm |
| Miglyol 840 | 0.360 Gm |
| Caprylic Acid | 0.050 Gm |
| Oleic Acid | 0.050 Gm |
| Klucel HF | 0.040 Gm |
| Total | 1.000 Gm |

The various ingredients of the formulations were mixed together in a glass apparatus. The drug was dissolved in this mixture. The gelling agent was added to this solution and the contents were mixed by using shear provided by a magnetic stirrer.

I claim:

1. A pharmaceutical composition for transdermal delivery consisting essentially of an effective transdermal amount of an active ingredient selected from a benzodiazepine and a benzodiazepine antagonist; and, as the essential transdermal absorption enhancers caprylic acid; ethanol; and oleic acid.

2. The composition of claim 1, wherein the ethanol is present in an amount of from about 10 to about 95 percent by weight of the composition; the caprylic acid is present in an amount of from about 1 to about 10 percent by weight of the composition and the oleic acid is present in an amount of from about 1 to about 10 percent by weight of the composition.

3. The composition of claim 1, wherein the benzodiazepine is diazepam, lorazepam or clonazepam.

4. The composition of claim 2, wherein the benzodiazepine is clonazepam.

5. The composition of claim 4, wherein the ethanol is present in an amount of from about 10 to about 90 percent by weight of the composition, the caprylic acid is present in an amount of from about 1 to about 10 percent by weight of the composition, and the oleic acid is present in an amount of from about 1 to about 10 percent by weight of the composition.

6. The composition of claim 5, wherein the ethanol is present in an amount of from about 50 to about 90 percent by weight of the composition, the caprylic acid is present in an amount of about 3 percent by weight of the composition and oleic acid is present in an amount of about 3 percent by weight of the composition.

7. The composition of claim 5, further comprising hydroxypropyl cellulose in an amount of from about 1 to about 4 percent by weight of the composition.

8. The composition of claim 7, further comprising silicon fluid.

9. The composition of claim 8, wherein the silicon fluid is present in an amount of from about 15 to about 25 percent by weight of the composition.

10. The composition of claim 9, wherein the silicon fluid is present in about 20 percent by weight of the composition.

11. The composition of claim 7, further comprising benzyl alcohol.

12. The composition of claim 11, wherein the benzyl alcohol is present in an amount of from about 5 to about 15 percent by weight of the composition.

13. The composition of claim 12, wherein the benzyl alcohol is present in an amount of about 10 percent by weight of the composition.

14. The composition of claim 7, further comprising transcutol.

15. The composition of claim 14, wherein the transcutol is present in an amount of from about 15 to about 30 percent by weight of the composition.

16. The composition of claim 15, wherein the transcutol is present in an amount of about 20 percent by weight of the composition.

17. The composition of claim 1, wherein the benzodiazepine antagonist is flumazenil.

18. The composition of claim 17, wherein the ethanol is present in an amount of from about 10 to about 95 percent by weight of the composition; caprylic acid is present in an amount of from about 1 to about 10 percent by weight of the composition; and the oleic acid is present in an amount of from about 1 to about 10 percent by weight of the composition.

19. The composition of claim 18, wherein the ethanol is present in an amount of from about 50 to about 70 percent by weight of the composition; the caprylic acid is present in an amount of from 3 to 5 percent by weight of the composition; and oleic acid is present in an amount of from about 3 to 5 percent by weight of the composition.

20. The composition of claim 18, further comprising hydroxypropyl cellulose in an amount of from about 1 to about 4 percent by weight of the composition.

21. The composition of claim 20, further comprising silicon fluid.

22. The composition of claim 21, wherein the silicon fluid is present in an amount of from about 15 to about 25 percent by weight of the composition.

23. The composition of claim 22, wherein the silicon fluid is present at about 20 percent by weight of the composition.

24. The composition of claim 20, further comprising dimethyl sulfoxide.

25. The composition of claim 24, wherein the dimethylsulfoxide is present in an amount of from about 1 to about 20 percent by weight of the composition.

26. The composition of claim 25, wherein the dimethylsulfoxide is present at about 2 percent by weight of the composition.

27. The composition of claim 20, further comprising acetone.

28. The composition of claim 27, wherein acetone is present in an amount of from about 15 to about 25 percent by weight of the composition.

29. The composition of claim 28, wherein the acetone is present at about 20 percent by weight of the composition.

30. The composition of claim 18, further comprising diethyl glycol monoethyl ether.

31. The composition of claim 30, wherein the diethyl glycol monoethyl ether is present in an amount of from about 15 to about 30 percent by weight of the composition.

32. The composition of claim 31, wherein the diethyl glycol monoethyl ether is present at about 20 percent by weight of the composition.

33. The composition of claim 18, further comprising caprylic/capric triglyceride.

34. The composition of claim 33, wherein the caprylic/capric triglyceride is present at about 36 percent by weight of the composition.

35. A pharmaceutical composition for transdermal delivery comprising an effective amount of flumazenil, caprylic acid, ethanol, oleic acid, silicon fluid and hydroxypropyl cellulose.

* * * * *